United States Patent [19]

Velez et al.

[11] Patent Number: 5,392,978
[45] Date of Patent: Feb. 28, 1995

[54] SURGICAL STAPLE AND ENDOSCOPIC STAPLER

[75] Inventors: Miguel A. Velez, Yorba Linda; Jaime S. Velez, Mission Viejo; Alvaro Velez, Laguna Niguel, all of Calif.

[73] Assignee: United States Surgical Corporation, Norwalk, Conn.

[21] Appl. No.: 137,884

[22] Filed: Oct. 15, 1993

Related U.S. Application Data

[63] Continuation of Ser. No. 929,483, Aug. 12, 1992, abandoned, which is a continuation of Ser. No. 653,029, Feb. 8, 1991, abandoned.

[51] Int. Cl.$^6$ .................... A61B 17/068; A61B 17/064
[52] U.S. Cl. ..................................... 227/177; 227/175; 227/19; 606/143; 411/471
[58] Field of Search ............... 227/175, 176, 177, 135, 227/120, 132, 19; 411/457–476; 606/142, 143

[56] References Cited

U.S. PATENT DOCUMENTS

| | | |
|---|---|---|
| Re. 28,932 | 8/1976 | Noiles et al. |
| Re. 33,362 | 10/1990 | Mongeon et al. |
| D. 277,785 | 2/1985 | Green . |
| D. 283,642 | 4/1986 | Gravener . |
| 389,660 | 9/1888 | Mandel et al. |
| 3,054,406 | 9/1962 | Usher . |
| 3,120,230 | 2/1964 | Skold . |
| 3,124,136 | 3/1964 | Usher . |
| 3,314,431 | 4/1967 | Smith, Jr. |
| 3,494,533 | 2/1970 | Green . |
| 3,631,707 | 1/1972 | Miller . |
| 3,643,851 | 2/1972 | Green et al. |
| 3,763,860 | 10/1973 | Clarke . |
| 3,777,538 | 12/1973 | Weatherly et al. |
| 3,837,555 | 9/1974 | Green . |
| 3,871,379 | 3/1975 | Clark . |
| 3,882,854 | 5/1975 | Hulka et al. |
| 3,955,581 | 5/1976 | Spasiano et al. |
| 4,014,492 | 3/1977 | Rothfuss . |
| 4,027,510 | 6/1977 | Hiltebrandt . |
| 4,038,987 | 8/1977 | Komiya . |

(List continued on next page.)

FOREIGN PATENT DOCUMENTS

| | | |
|---|---|---|
| 0085930 | 8/1983 | European Pat. Off. |
| 2330182 | 1/1975 | Germany . |
| 2703529 | 8/1978 | Germany . |
| 3802651 | 3/1989 | Germany . |
| WO90/03763 | 6/1989 | WIPO . |

OTHER PUBLICATIONS

Publication Entitled Shape Memory Alloys from Scientific American Nov. 1979.

(List continued on next page.)

Primary Examiner—Eugenia Jones
Assistant Examiner—Allan M. Schrock

[57] ABSTRACT

An improved staple for use with an endoscopic stapler has arms which are curved toward each other such that the staple may be crimped so as to cause the arms to move toward each other and thereby lock the staple into place. This crimping action substantially mitigates the likelihood of the staple inadvertently pulling out. The staple also has an abutment bend formed therein to serve as a detent and thereby secure the staple within the jaws of an endoscopic stapler. An endoscopic stapler for effecting use of the improved staple is also disclosed. The endoscopic stapler generally comprises an elongate tubular section which may be inserted through an endoscopic incision into a human body; a handle portion having a trigger for effecting the stapling process; a pair of jaws disposed at the distal end of the elongate tube for positioning and crimping a staple in place; a feed mechanism for advancing a series of staples to the jaws; and a means for selectively adjusting the amount of crimp imparted to the staple. The improved staple and endoscopic stapler of the present invention permit a surgeon to rapidly secure anatomical body portions and/or therapeutic devices in place within the human body without requiring an incision in excess of approximately 1 centimeter.

14 Claims, 10 Drawing Sheets

U.S. PATENT DOCUMENTS

| | | |
|---|---|---|
| 4,043,504 | 8/1977 | Hueill . |
| 4,064,881 | 12/1977 | Meredith . |
| 4,127,227 | 11/1978 | Green . |
| 4,152,920 | 5/1979 | Green . |
| 4,166,466 | 9/1979 | Jarvik . |
| 4,169,476 | 10/1979 | Hiltebrandt . |
| 4,196,836 | 4/1980 | Becht . |
| 4,204,623 | 5/1980 | Green . |
| 4,207,873 | 6/1980 | Kruy . |
| 4,228,895 | 10/1980 | Larkin . |
| 4,246,903 | 1/1981 | Larkin . |
| 4,256,251 | 3/1981 | Moshofsky . |
| 4,261,244 | 4/1981 | Becht et al. . |
| 4,316,468 | 2/1982 | Klieman et al. . |
| 4,317,535 | 3/1982 | Huftel et al. . |
| 4,321,002 | 3/1982 | Froehlich . |
| 4,325,376 | 4/1982 | Klieman et al. . |
| 4,347,847 | 9/1982 | Usher . |
| 4,349,028 | 9/1982 | Green ................................. 227/175 |
| 4,375,866 | 3/1983 | Giersch et al. . |
| 4,394,864 | 7/1983 | Sandhaus ........................... 606/142 |
| 4,399,810 | 8/1983 | Samuels et al. . |
| 4,403,693 | 9/1983 | Froehlich ............................ 227/19 |
| 4,406,392 | 9/1983 | Campbell et al. . |
| 4,407,286 | 10/1983 | Noiles et al. . |
| 4,412,539 | 11/1983 | Jarvik . |
| 4,437,847 | 9/1982 | Usher . |
| 4,452,245 | 6/1984 | Usher . |
| 4,452,357 | 6/1984 | Klieman et al. . |
| 4,470,532 | 9/1984 | Froehlich . |
| 4,485,816 | 12/1984 | Krumme et al. . |
| 4,489,875 | 12/1984 | Crawford et al. . |
| 4,492,232 | 1/1985 | Green . |
| 4,496,090 | 1/1985 | Crevier et al. . |
| 4,505,273 | 3/1985 | Braun et al. . |
| 4,509,518 | 4/1985 | McGarry et al. . |
| 4,512,345 | 4/1985 | Green . |
| 4,519,532 | 5/1985 | Foslien . |
| 4,520,817 | 6/1985 | Green . |
| 4,523,695 | 6/1985 | Braun et al. . |
| 4,523,707 | 6/1985 | Blake, III et al. . |
| 4,526,174 | 7/1985 | Froehlich . |
| 4,527,724 | 1/1985 | Chow et al. . |
| 4,532,927 | 8/1985 | Miksza, Jr. . |
| 4,550,715 | 12/1985 | Santangelo et al. . |
| 4,556,058 | 12/1985 | Green . |
| 4,557,263 | 12/1985 | Green . |
| 4,562,839 | 1/1986 | Blake, III et al. . |
| 4,566,620 | 1/1986 | Green et al. . |
| 4,576,165 | 3/1986 | Green et al. . |
| 4,583,670 | 4/1986 | Alvarado . |
| 4,591,086 | 5/1986 | Campbell et al. . |
| 4,592,498 | 6/1986 | Braun et al. . |
| 4,607,638 | 8/1986 | Crainich . |
| 4,610,251 | 9/1986 | Kumar . |
| 4,610,383 | 9/1986 | Rothfuss et al. . |
| 4,616,650 | 10/1986 | Green et al. . |
| 4,618,086 | 10/1986 | Li et al. . |
| 4,619,391 | 10/1986 | Sharkany et al. . |
| 4,624,254 | 11/1986 | McGarry et al. . |
| 4,634,035 | 1/1987 | Li et al. .................................. 227/19 |
| 4,655,221 | 4/1987 | Devereux . |
| 4,662,373 | 5/1987 | Montgomery et al. . |
| 4,662,555 | 5/1987 | Thornton . |
| 4,664,305 | 5/1987 | Blake, III et al. . |
| 4,665,906 | 5/1987 | Jervis . |
| 4,671,279 | 6/1987 | Hill . |
| 4,674,504 | 7/1987 | Klieman et al. . |
| 4,688,555 | 8/1987 | Wardle . |
| 4,691,853 | 9/1987 | Storace . |
| 4,706,655 | 11/1987 | Krauter . |
| 4,712,549 | 12/1987 | Peters et al. . |
| 4,719,917 | 1/1988 | Barrows et al. . |
| 4,728,020 | 3/1988 | Green et al. . |
| 4,747,531 | 5/1988 | Brinkerhoff et al. . |
| 4,763,669 | 8/1988 | Jaeger . |
| 4,784,137 | 11/1988 | Kulik et al. . |
| 4,787,387 | 11/1988 | Burbank, III et al. ............... 227/176 |
| 4,789,090 | 12/1988 | Blake, III . |
| 4,802,478 | 2/1989 | Powell . |
| 4,807,628 | 2/1989 | Peters et al. . |
| 4,821,939 | 4/1989 | Green . |
| 4,821,942 | 4/1989 | Richards et al. ..................... 227/132 |
| 4,838,884 | 6/1989 | Dumican et al. . |
| 4,841,888 | 6/1989 | Mills et al. . |

(List continued on next page.)

OTHER PUBLICATIONS

M-D-D-I Report, Sep. 1991 Ethicon Endoscopic Staple for Hernia Repair.

Information Booklet for Auto Suture® Multifire Premium198 Disposable Skin Stapler and Disposable Loading Unit.

Publication Entitled "A Quick Stapler Tie-Over Fixation For Skin Grafts", by Haim Y. Kaplan, M.D. Ann. Plast. Surg., 22:173, 1989, pp. 173–174.

Publication Entitled "A Rapid and Effective Method of Skin Graft Stabilization in Burned Children", by J. B.

(List continued on next page.)

U.S. PATENT DOCUMENTS

| | | |
|---|---|---|
| 4,850,355 | 7/1989 | Brooks et al. . |
| 4,858,608 | 8/1989 | McQuilkin . |
| 4,872,454 | 10/1989 | Hasson . |
| 4,874,122 | 10/1989 | Froelich et al. . |
| 4,880,015 | 11/1989 | Nierman . |
| 4,899,745 | 2/1990 | Laboureau et al. . |
| 4,919,112 | 4/1990 | Siegmund . |
| 4,919,152 | 4/1990 | Ger . |
| 4,919,320 | 4/1990 | Storace . |
| 4,934,364 | 6/1990 | Green . |
| 4,944,443 | 7/1990 | Oddsen et al. . |
| 4,951,861 | 8/1990 | Shulze et al. . |
| 4,978,049 | 12/1990 | Green ................... 227/178 |
| 4,997,436 | 3/1991 | Oberlander . |
| 5,002,551 | 3/1991 | Linsky et al. . |
| 5,015,249 | 5/1991 | Nakao et al. . |
| 5,040,715 | 8/1991 | Green et al. . |
| 5,047,038 | 9/1991 | Peters et al. . |
| 5,049,153 | 9/1991 | Nakao et al. . |
| 5,071,430 | 12/1991 | de Salis et al. . |
| 5,084,057 | 1/1992 | Green et al. . |
| 5,100,420 | 3/1992 | Green et al. . |
| 5,125,553 | 6/1992 | Oddsen et al. . |
| 5,174,487 | 12/1992 | Rothfuss et al. . |
| 5,222,975 | 6/1993 | Crainich . |
| 5,246,156 | 9/1993 | Rothfuss et al. . |
| 5,289,963 | 3/1994 | McGarry et al. . |

OTHER PUBLICATIONS

Boyd et al., The Hospital For Sick Children, Toronto, Canada, 1982, pp. 400–401.

Publication Entitled "A Simple Bolster Technique For Skin Grafting", by Henry T. Hoffman, M.D. and Michael LaRouere, M.D., Department of Otolarynogology, University of Michigan, Laryngoscope 99, May 1989, p. 558.

Article Swain, C. P., Mills, T. N. "An Endoscopic Sewing Machine", *Gastrointestinal Endoscope*, 1986, vol. 32, No. 1, pp. 36–38.

Article, Swain, C. P. Brown, G. J. and Mills, T. N. "An Endoscopic Stapling Device: The Development of a New Flexible Endoscopically Controlled Device for Placing Multiple Transmural Staples in Gastrointestinal Tissue", *Gastrointestinal Endoscopy*, 1989, vol. 35, No. 4, pp. 338–339.

"Laparascopic Sterilization with Spring Clips" by Jaroslav Hulka, M.D.

Information Booklet for Auto Suture* Premium Surgiclip* titanium disposable automatic clip appliers.

Information Booklet for Auto Suture* skin and fascia surgical stapling instruments and disposable loading units.

SURGICAL STAPLE AND ENDOSCOPIC STAPLER

This is a continuation of application Ser. No. 07/929,483, filed on Aug. 12, 1992, now abandoned, which is a continuation of application Ser. No. 07/653,029, filed on Feb. 8, 1991, now abandoned.

FIELD OF THE INVENTION

The present invention relates generally to medical equipment and more particularly to an improved surgical staple which resists inadvertent pullout and to a device which may be inserted into the body through a small incision and subsequently utilized to insert the improved surgical staple into anatomical body portions and/or therapeutic devices within the body.

BACKGROUND OF THE INVENTION

The development of modern endoscopic instrumentation has significantly affected the manner in which many surgical procedures are performed. Indeed, many procedures which have traditionally required large surgical incisions (e.g. laparotomy) may now be performed endoscopically, by inserting an endoscopic viewing device (e.g. a laparoscope, arthroscope, bronchoscope, etc.) along with various surgical instruments through natural body openings or small incisions.

The development of modern endoscopic surgical procedures has enabled surgeons to perform major operative procedures at relatively low risk, without the need for deep muscle relaxation and with minimal blood loss and minimal post-operative discomfort.

In particular, recent advancements in laparoscopic technology have enabled surgeons to perform various intra-abdominal surgical procedures through one or more relatively small (e.g. 1 cm) laparoscopy incisions rather than through the traditional, relatively large (e.g. 5–20 cm) laparotomy incision.

In accordance with standard laparoscopic technique, an inflation needle is initially inserted into the peritoneum and carbon dioxide is passed therein to create a distended pneumoperitoneum. Thereafter, a small periumbilical incision is formed and a primary portal or trocar is inserted through such periumbilical incision into the distended peritoneum. The laparoscope is then inserted into the peritoneum through the primary umbilical trocar. One or more secondary trocars or accessory portals may also be inserted through one or more secondary incisions or puncture wounds formed in the abdominal wall. Such secondary trocars or accessory portals are generally used for passage of blunt forceps, cannulas and other instruments into the abdomen.

After such instruments have been inserted through the accessory portals, the instruments are used to carry out the desired surgical excision and/or manipulation of organs and tissues within the abdomen while the surgeon views the operative site through the previously inserted laparoscope. Any surgically excised tissue or other material which is to be removed during the surgical procedure must then be extricated from the body, preferably by extraction through one of the previously made laparoscopy portal incisions.

For example, a common hernia repair may be effected endoscopically by suturing a fabric mesh in place over the wound to provide support to the weakened area during the healing process. This is typically accomplished by using forceps or other surgical tools to manipulate a threaded needle through a trocar in order to form the sutures. The suturing process commonly is simultaneously observed through an endoscope inserted through a separate trocar. To accomplish suturing, the threaded needle must be passed through the trocar and into the inflated abdomen or pneumoperitoneum; the sutures must be formed; a knot must be tied and the thread cut when suturing is complete; and finally the needle and remaining thread must be extracted through the trocar.

Although laparoscopic procedures have evolved to the point when internal incisions and the like may be repaired by manipulating a threaded needle endoscopically to form sutures, the ultimate success and feasibility of many such surgical procedures is dependent upon the ability of the surgeon to perform the procedure in a limited amount of time. Manual endoscopic suturing is a time-consuming task requiring a great deal of skill.

Similar problems exist in suturing anatomical body portions and/or therapeutic devices, e.g. a fabric mesh, in other contemporary surgical procedures, including those which are performed through natural body openings such as the oral cavity, urethra, vagina, rectum, etc.

Laparoscopy has, for some time, been used in the treatment of gynecologic diseases. More recently, and largely due to the development of highly efficient laser cutting and coagulation devices, laparoscopy has shown promise as a modality for performing various other general surgical procedures which had heretofore been performed through relatively large (e.g. 5–40 cm) laparotomy incisions. Indeed, frequently performed intra-abdominal surgical procedures such as cholecystectomy and appendectomy may now be approached with the laparoscope through a relatively small (e.g. 1 cm) abdominal puncture. The feasibility of performing such operations is, however, in part dependent upon the ability of the surgeon to close wounds, suture therapeutic devices in place, and suture anatomical body portions in place.

Any endoscopic suturing or stapling must take place through a trocar inserted into one of the previously made laparoscopy portal incisions. Thus contemporary surgical staplers cannot be substituted for suturing since they cannot be inserted through the opening of a trocar.

Prior art surgical staples generally suffer from the deficiency that, after stapling, they are undesirably prone to being pulled out of the anatomical body portion and/or therapeutic device into which they have been disposed. Such prior art surgical staples have straight arms which are not crimped toward each other. Thus, such prior art staples lack a mechanism to prevent their moving away from and out of engagement with the anatomical body portion and/or therapeutic device into which they have been inserted. Movement of the stapled anatomical body portions and/or therapeutic devices, as well as tension placed thereupon, may cause such prior art staples to be pulled out.

In view of the problems associated with endoscopic suturing and similar surgical procedures, i.e. stapling, there exists in the art the need for an improved staple which is not substantially subject to being inadvertently pulled out and for an instrument which may be passed into the pneumoperitoneum or the like through a standard (e.g. 1 cm) laparoscopy incision to effect stapling of anatomical body portions and/or therapeutic devices.

SUMMARY OF THE INVENTION

The present invention specifically addresses and alleviates the above mentioned deficiencies associated in the prior art. More particularly, the present invention comprises an improved staple and an endoscopic stapler. The staple has arms which are curved toward each other such that the staple may be crimped so as to cause the arms to move toward each other and thereby lock the staple into place. This crimping action substantially mitigates the likelihood of the staple being inadvertently pulled out or extracted. The staple also has an abutting bend formed such that compression or squeezing together of the arms of leading or nested staples disposed serially within an endoscopic stapler is prevented and the occurrences of jamming are reduced. The abutment or abutting bend also prevents the improved staple from slipping out of the jaws of the endoscopic stapler.

The endoscopic stapler for effecting use of the improved surgical staple generally comprises an elongate tubular section which may be inserted through a standard (e.g. 1 cm) laparoscopy incision into a human body; a handle portion having a trigger for effecting the stapling process; a pair of extensible jaws disposed at the distal end of the elongate tube for positioning and crimping a staple in place; a feed mechanism for advancing a series of staples to the jaws; and a means for selectively adjusting the amount of crimp imparted to the staple.

The improved staple and endoscopic stapler of the present invention permit a surgeon to rapidly secure anatomical body portions and/or therapeutic devices in place within the human body without requiring an incision in excess of approximately 1 centimeter.

DETAILED DESCRIPTION OF THE INVENTION

Figure 1:
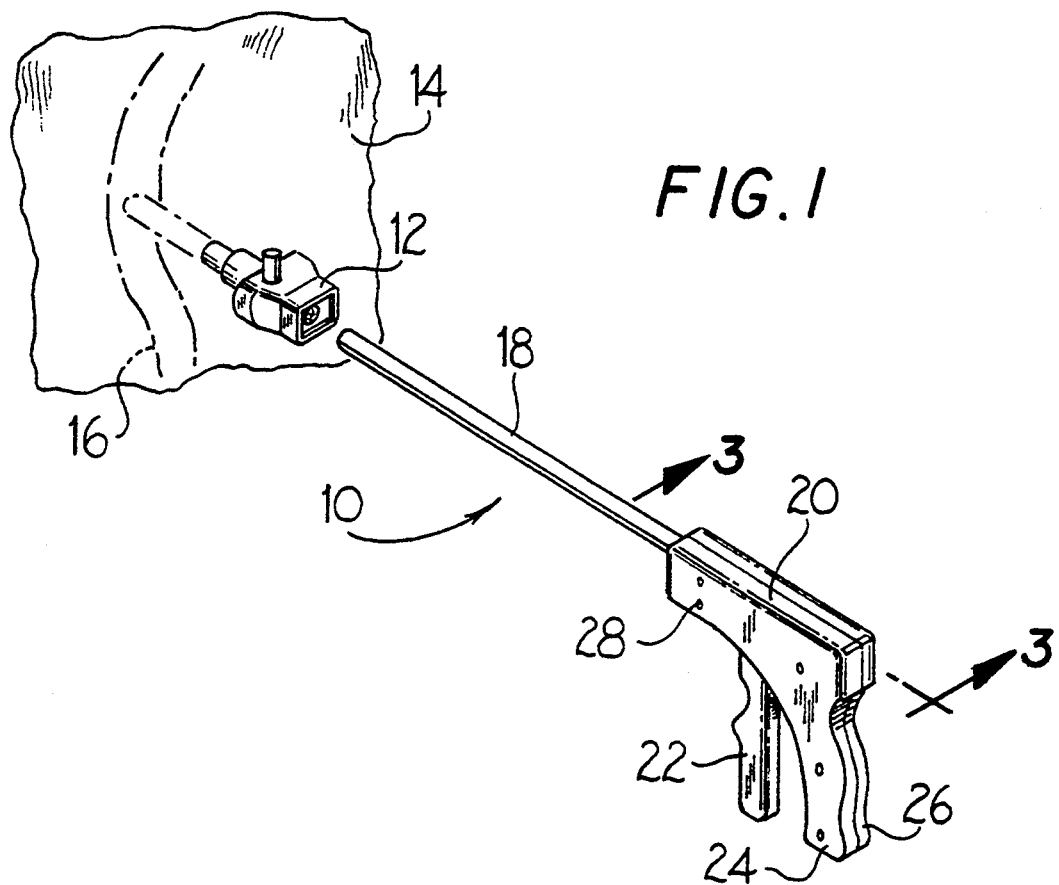
FIG. 1 is a perspective view of the endoscopic stapler of the present invention positioned to be inserted through a trocar and into a human abdomen.

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The present invention may be used in any type of endoscopic or other surgical procedure wherein it is desired to staple anatomical body portions and/or therapeutic devices in place through a relatively small opening. Because the present invention is particularly applicable to intra-abdominal laparoscopic surgical procedures, the invention will be described herein with particular reference thereto. The making of such particular reference to laparoscopic surgical procedures shall not, however, constitute a limitation on the overall description and intended application of the present invention. In fact, in addition to intra-abdominal laparoscopic procedures, the present invention may be usable in many other types of procedures.

The improved surgical staple of the present invention is illustrated in FIGS. 4, 5, and 8-13. The endoscopic stapler of the present invention is illustrated in FIGS. 1 through 13.

Referring now to FIGS. 4-13 the improved staple of the present invention comprises a straight elongate base or rear portion 106 and proximal bends 108 attaching first 112 and second 114 arms to the base 106. An abutment bend 102 is formed upon each arm 112 and 114 such that an outboard bump or bulge is formed thereby in the outboard surface of each arm 112 and 114. A distal bend 110 is also formed in each arm 112 and 114 such that distal ends or tips 104 bend toward each other. The staple 100 is preferably fabricated of stainless steel although those skilled in the art will recognize that other biologically compatible materials having similar characteristics are likewise suitable.

The improved staple 100 of the present invention provides a staple which may be used in an endoscopic stapler and which is substantially less subject to being inadvertently pulled out than prior art staples.

The staple 100 is sized to be received within an endoscopic stapler. The base 106 generally has a length of less than 1 cm, with a length of 4 to 6 mm being preferred.

Figure 8:
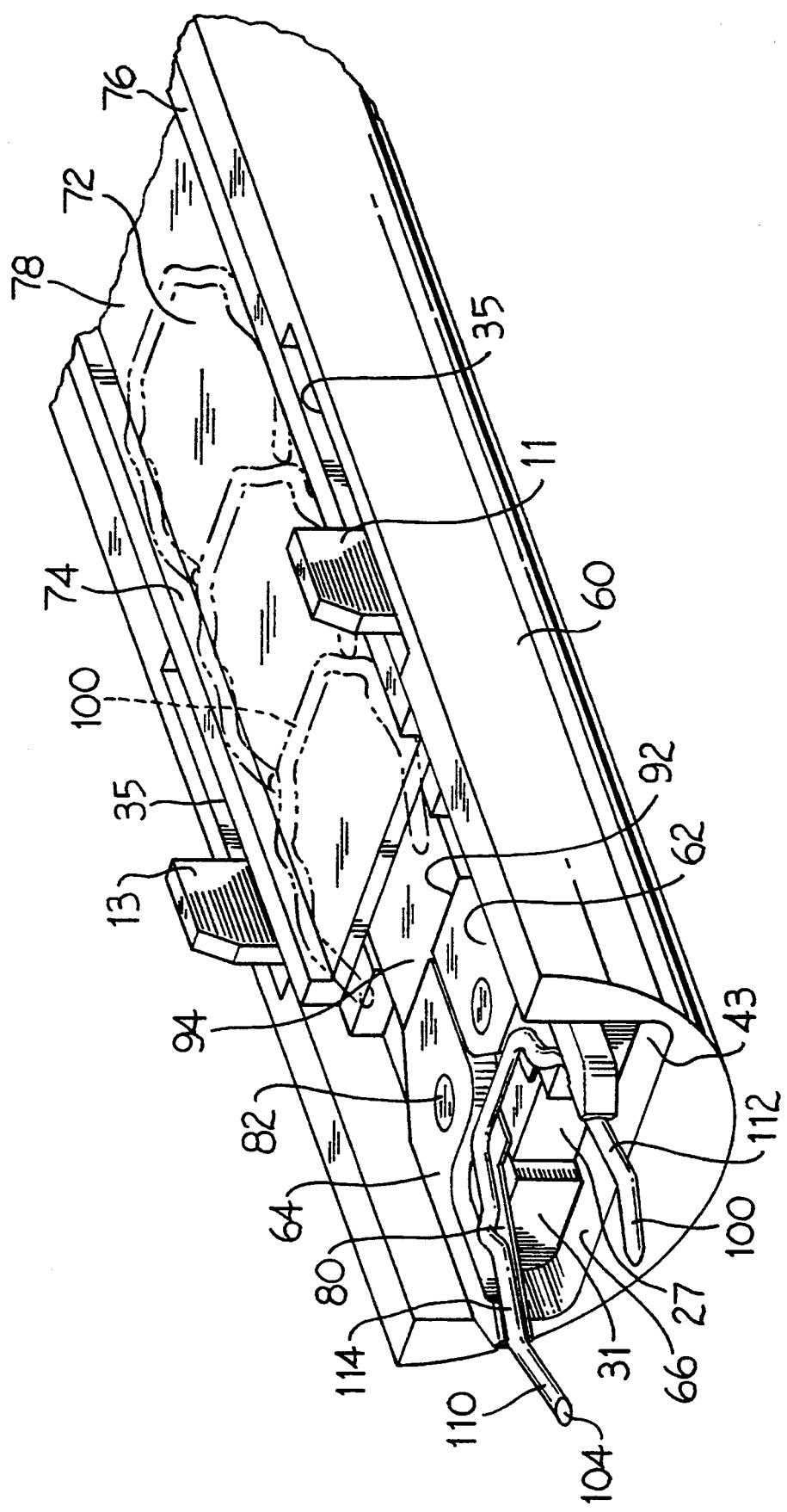
FIG. 8 is an enlarged sectional perspective view of the lower half of the distal end of the elongate tube of the endoscopic stapler of the present invention showing the extensible jaws partially extended as during the insertion of a staple and showing a nested series of staples disposed therein.
Figure 9:
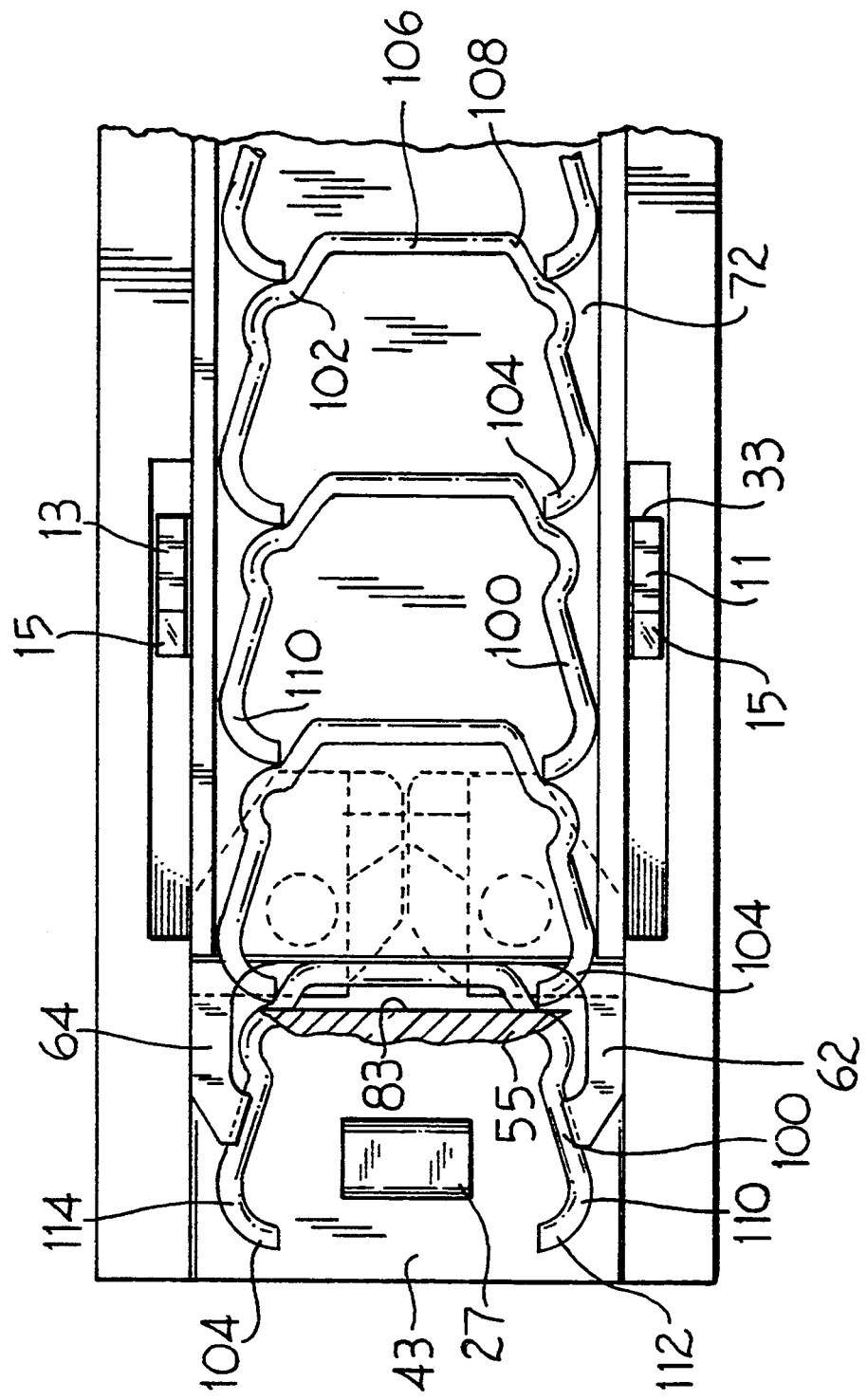
FIG. 9 is a top plan view of the lower half of the distal end portion of FIG. 8 showing the extensible jaws disposed in their retracted position.
Figure 11:
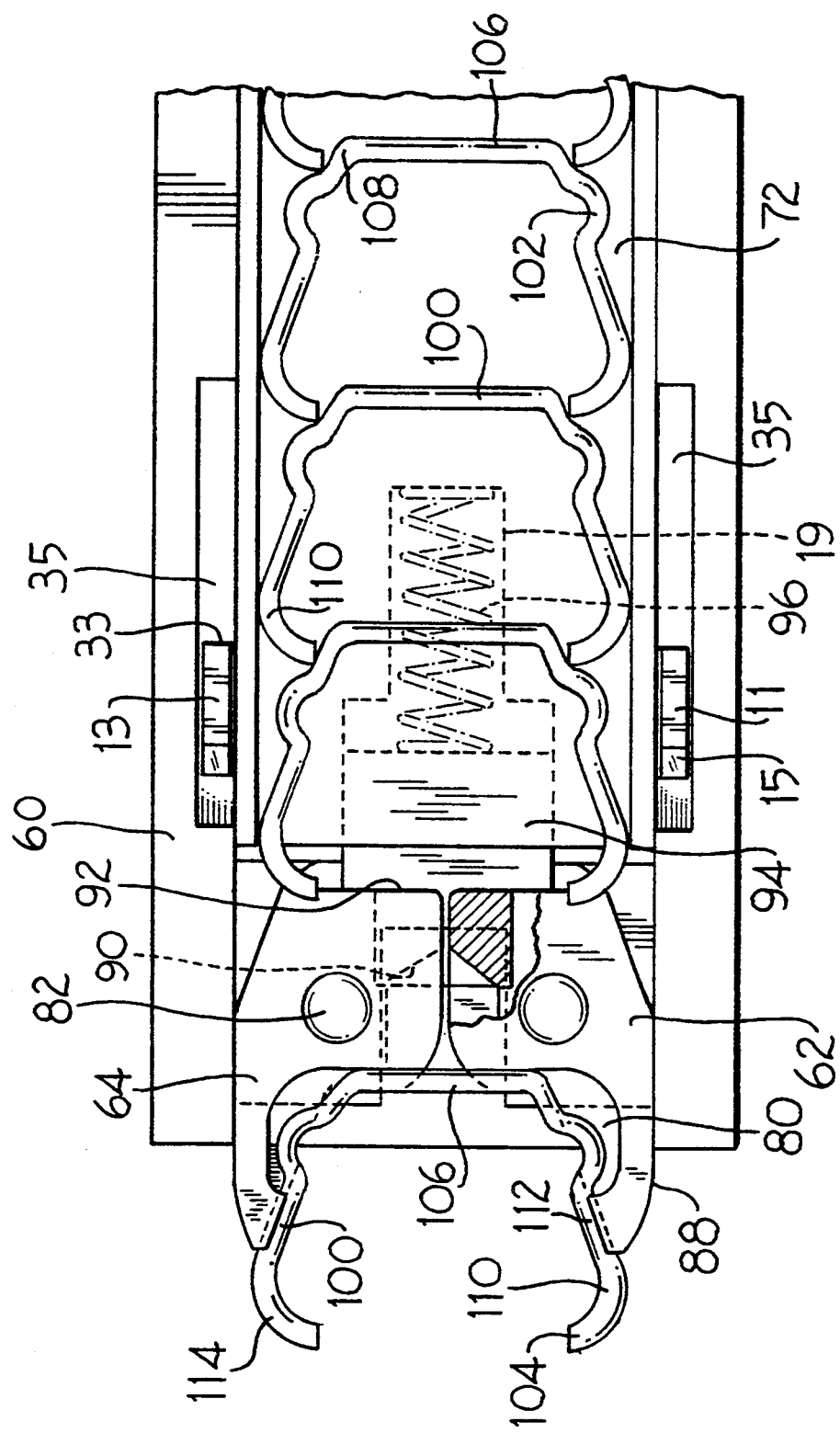
FIG. 11 is a top plan view of the lower half of the distal end portion of the endoscopic stapler of FIG. 8 showing the extensible jaws disposed in their extended position.

Abutment bends 102 are provided to prevent subsequent staples 100 from "riding up" on preceding staples 100 as they are urged forward in a nested series (as best shown in FIGS. 8, 9, and 11). Without the abutment bend subsequent staples 100 may tend to urge the arms 112 and 114 of preceding staples 100 together, i.e. as when they are crimped, as the staples 100 are urged toward the distal end of the endoscopic stapler, thereby distorting the shape of the preceding staples 100 and potentially jamming the endoscopic stapler. The abutment bend 102 maintains the positioning of the tips 104 of subsequent staples 100 proximate the bases 106 of preceding staples 100 such that the arms 112 and 114 of the subsequent staples 100 do not tend to ride up along the arms 112 and 114 of the preceding staples 100. Thus, performance and reliability of the improved staple 100 is enhanced.

The abutment bends 102 also prevent the staples 100 from inadvertently slipping out of the jaws 62 and 64 of an endoscopic stapler. This is necessary because of the generally "V" shaped configuration of the staples 100 which would otherwise be difficult to grasp from the sides. As can be seen in FIG. 8, the abutment bends 102 contact the jaws 62 and 64 and prevent the staple 100 from moving distally prior to being crimped.

The distal bend 110 formed in each arm 112 and 114 forms a preferential bending site which causes the tips 104 to curve toward each other such that crimping of the arms 112 and 114 brings the tips 104 closer together. Thus, crimping the improved staple 100 of the present invention firmly secures the staple 100 in place such that the probability of the staple 100 being inadvertently pulled out of the anatomical body portion or therapeutic device into which it is inserted is substantially reduced.

The distal ends or tips 104 of each arm 112 and 114 may be beveled, cut at an angle, or sharpened to improve the ability of the improved staple 100 to penetrate anatomical body portions and/or therapeutic devices.

As the staples 100 are crimped into place they tend to draw the two sides of a wound together, thus closing the wound in a desirable manner. Additionally, crimping causes the staple 100 to pull layered structures together. For example, when a fabric mesh is being stapled 100 to an anatomical body portion, stapling causes the staple 100 to pull the fabric mesh into tighter contact with the anatomical body portion as the staple 100 is crimped. Thus, not only does the improved surgical staple 100 of the present invention reduce the probability of the staple 100 being inadvertently pulled out, but also tends to close wounds and improve the contact of therapeutic devices with anatomical body portions in a desirable manner.

Referring now to FIG. 1, the endoscopic stapler for dispensing the improved staples 100 of the present invention is comprised generally of an elongate tubular section 18, sized to be inserted through a trocar 12 into a body 14; and a handle 20 having a trigger 22 pivotally attached thereto, for effecting actuation of the stapler mechanism. The handle 20 is further comprised of first 24 and second 26 body halves.

Figure 2:
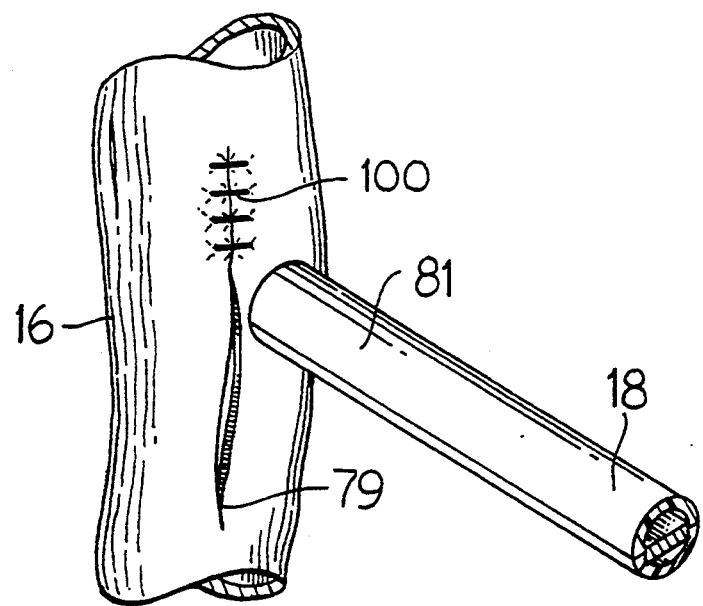
FIG. 2 is an enlarged perspective view of the distal end of the endoscopic stapler of FIG. 1 in the process of stapling a wound closed.

Referring now to FIG. 2, the distal portion 81 of the tubular member 18 of the endoscopic stapler 10 is illustrated in the process of inserting and crimping staples into a wound 79 of an anatomical body portion 16.

As can be seen, a series or array of staples 100 are inserted such that they close the wound 79 and hold the two sides of the wound 79 in position for healing. As mentioned above, the crimping process tends to draw the sides of the wound 79 together such that desirable contact is maintained and healing is facilitated.

Figure 3:
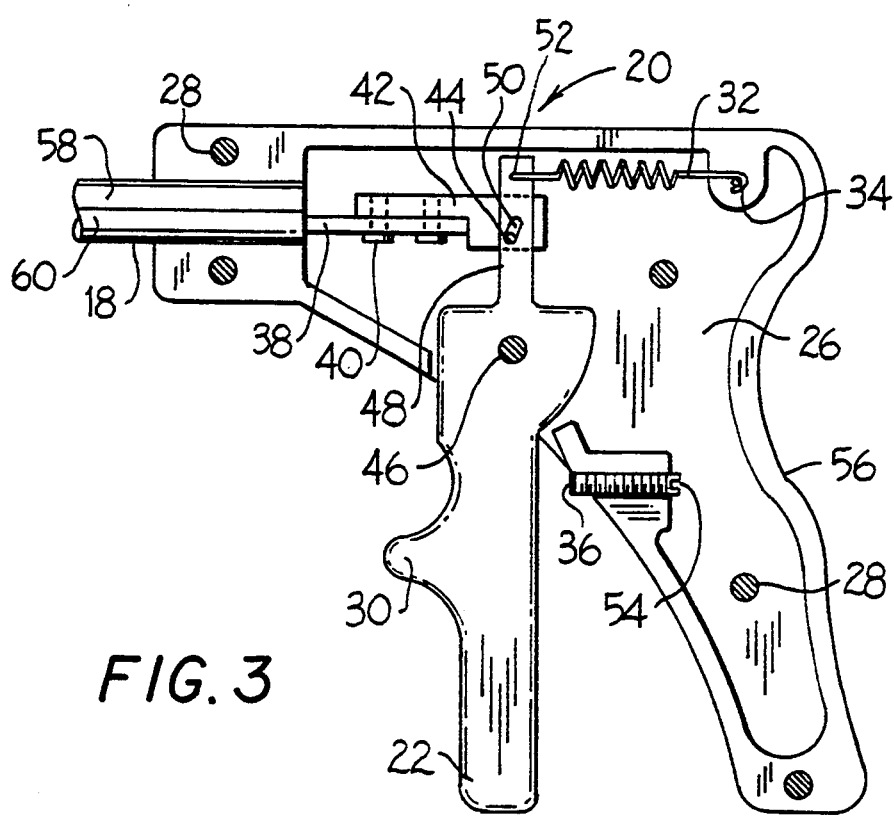
FIG. 3 is an enlarged cross sectional view of the handle of the endoscopic stapler of FIG. 1.

Referring now to FIG. 3, the actuation mechanism disposed within the handle 20 is shown. The actuation mechanism comprises those components which facilitate control of the stapling process, i.e. the trigger and linkage mechanisms. The trigger 22 has a finger stop 30 to improve the grip thereof and thus provide better control. The trigger 22 pivots about trigger pivot post 46 such that pulling the trigger 22 causes integral trigger arm 48 to move forward against the biasing of return spring 32. Return spring 32 is attached to the trigger arm 48 at aperture 52 and is attached to the second handle body half 26 by the spring post 34. The return spring 32 thus urges the trigger 22 into an extended or non-actuated position.

A push rod attachment block 42 has a post 44 formed thereon which extends through a slot 50 formed in the trigger arm 48 such that forward motion of the trigger arm 48 causes similar forward motion of the push rod attachment block 42. The slot 50 permits the push rod attachment block 42 to remain in substantially the same horizontal plane as it travels forward. Fasteners or screws 40 attach the push rod attachment block 42 to a push rod 38 which extends substantially the length of the tubular member 18.

A trigger stop screw 36 extends from the forward portion of the handle such that it limits the rearward travel of the trigger 22. A screwdriver slot 54 formed in the rearmost portion of the trigger stop screw 36 permits adjustment thereof through aperture 56 formed in the handle 20.

The tubular member 18 is comprised of upper 58, and lower 60 housings. Fasteners or screws 28 attach the first 24 and second 26 handle body halves together.

Figure 4:
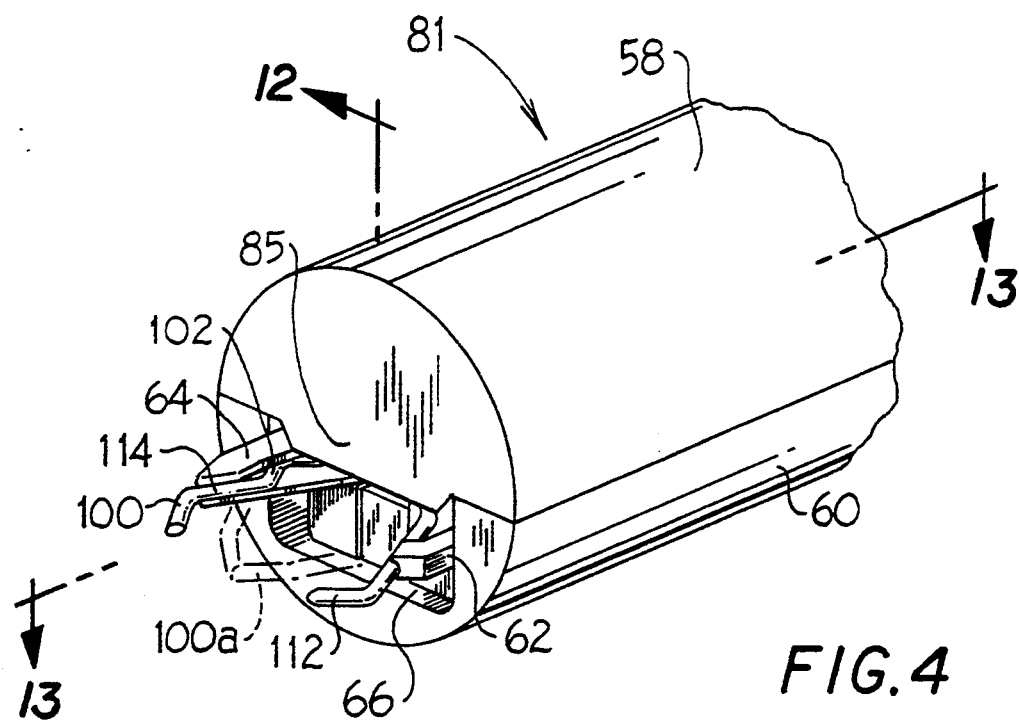
FIG. 4 is an enlarged perspective view of the distal end of the endoscopic stapler of FIG. 1.
Figure 5:
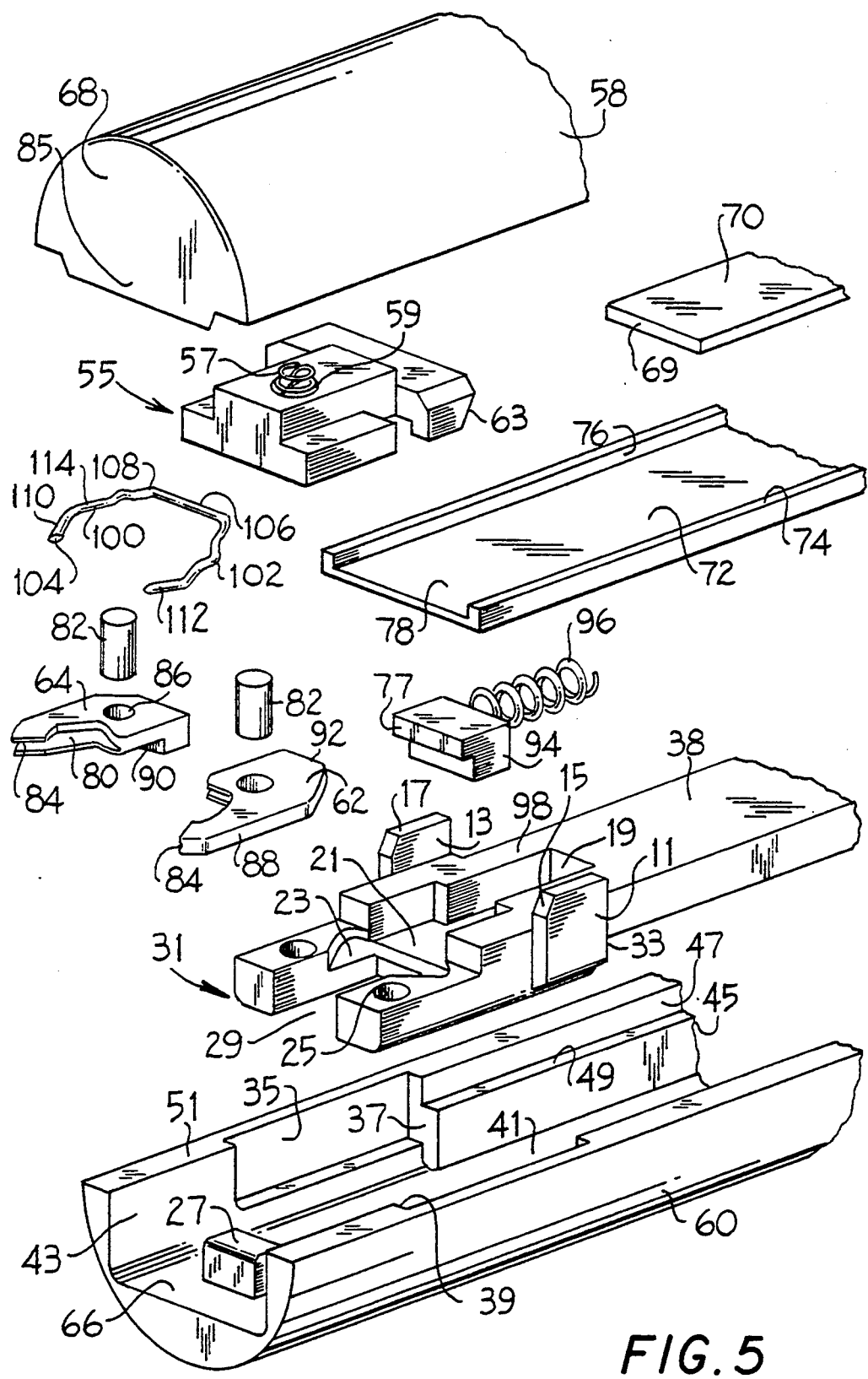
FIG. 5 is an exploded perspective view of the distal end of the endoscopic stapler of FIG. 4.

Referring now to FIG. 4, an enlarged view of the distal portion 81 of the tubular member 18 is shown. Right 62 and left 64 jaws extend from an opening 66 formed in the lower tubular member housing 60 and hold an improved staple 100 of the present invention such that lit may be inserted and crimped into place. A lap 85 extends downward from the upper housind 58. The abutment bends 102 formed in the staple 100 prevent it from sliding forward, out of the jaws 62 and 64. A crimped staple 100A is shown in phantom. Referring now to FIG. 5, an exploded view of the distal portion 81 of the tubular member 18 is shown. Upper 58 and lower 60 housings contain and support the mechanisms for feeding, inserting and crimping the improved surgical staples 100. The upper housing 58 has an end wall 68 formed at the distal most portion thereof. The lower housing 60 has an opening 66 formed in the distal end thereof and continuous with a channel 43 formed therethrough and also has an upper surface 51. A jaw closing cam 27 extends upward from the lower surface 41 of the channel 43 proximate the opening 66. Push rod arm recesses 35 having rear surfaces 37 and forward surfaces 39 are formed in the lower housing 60. A track 45 having a lower surface 49 is formed substantially along channel 43.

A jaw carrier 31 is formed upon the distal portion 98 of the push rod 38 such that the jaw carrier 31 extends toward the opening 66 of the lower housing 60 as the push rod 38 moves forward when the trigger 22 is actuated or depressed. The jaw carrier 31 comprises a jaw closing cam slot 29 formed in the distal most end thereof, pivot post apertures 25 formed on either side of the jaw closing cam slot 29, and a jaw recess 23 disposed proximate the pivot post apertures 25 and configured to receive a portion of the jaws 62 and 64. A jaw opening cam recess 21 is configured to receive a jaw opening cam 94 which is spring biased forward by coil spring 96. Cam spring recess 19 is disposed proximal the jaw opening cam recess 21 and receives the coil spring 96. Right 11 and left 13 push rod arms extend upward from the sides of the jaw carrier 31 and have camming surfaces 15 and upper surfaces 17 formed upon the forward upper portions thereof. Both push rod arms 11 and 13 have rear surfaces 33 (better shown in FIGS. 9 and 10) which will contact the rear surface 37 of the push rod arm recess 35 when the push rod 38 is disposed in its rearmost position as when the trigger 22 is not depressed or actuated.

Figure 7:
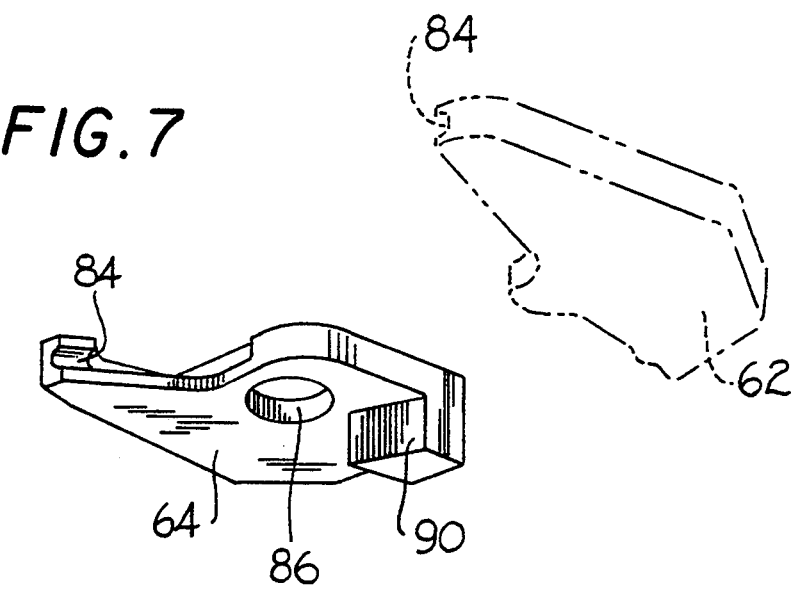
FIG. 7 is a perspective view of the extensible jaws of FIG. 5 having the right jaw drawn in phantom and showing the undersides thereof.

With particular reference to FIGS. 5 and 7, the jaws 62 and 64 have outboard surfaces 88, opening camming surfaces 92 (better shown in FIGS. 11 and 13), a staple platform 80, staple support grooves 84, closure camming surfaces 90 and pivot post apertures formed thereon. Jaw pivot posts 82 are received by the jaw pivot post apertures 86 and the jaw carrier pivot post apertures 25 such that the jaws 62 and 64 may pivot relative to the jaw carrier 31.

The spring biased jaw opening cam 94 has an abutment surface 77 configured to abut the opening camming surface 92 of the jaws 62 and 64 such that they are cammed toward the open or non-crimping position thereof. The outboard surfaces 88 of the jaws 62 and 64 abut the channel 43 in the lower housing 60 when the jaw carrier 31 is not extended. The closure camming surfaces 90 of the jaws 62 and 64 abut the jaw closing cam 27 such that the jaws are urged into a closed or crimped position when the jaw carrier 31 is extended as when the trigger 22 is depressed or actuated. Staple platforms 80 is configured to receive and support an improved staple 100 of the present invention. The staple support grooves 84 capture a portion of the arms 112 and 114 to prevent inadvertent release of the staple from the jaws 62 and 64.

With particular reference to FIGS. 5, 8, 9 and 11 a staple tray 72 is sized to be disposed within the track 45 in the lower housing 60 and has a channel 78 which is sized and configured to receive a series of nested improved surgical staples 100 of the present invention such that the staples 100 may be fed to jaws 62 and 64. Right 74 and left 76 guide members guide the series of staples 100 and maintain their positions as they are fed toward the jaws 62 and 64.

A staple pressure plate 55 has camming surfaces 63 configured to contact the camming surfaces 15 of the push rod arms 11 and 13 such that the staple pressure plate 55 will be cammed upward when the push rod 38 is disposed in its forward most position as when the trigger 22 is depressed or actuated. A recess 59 formed in the staple pressure plate 55 receives a coil spring 57 which biases the staple pressure plate 55 downward.

Figure 6:
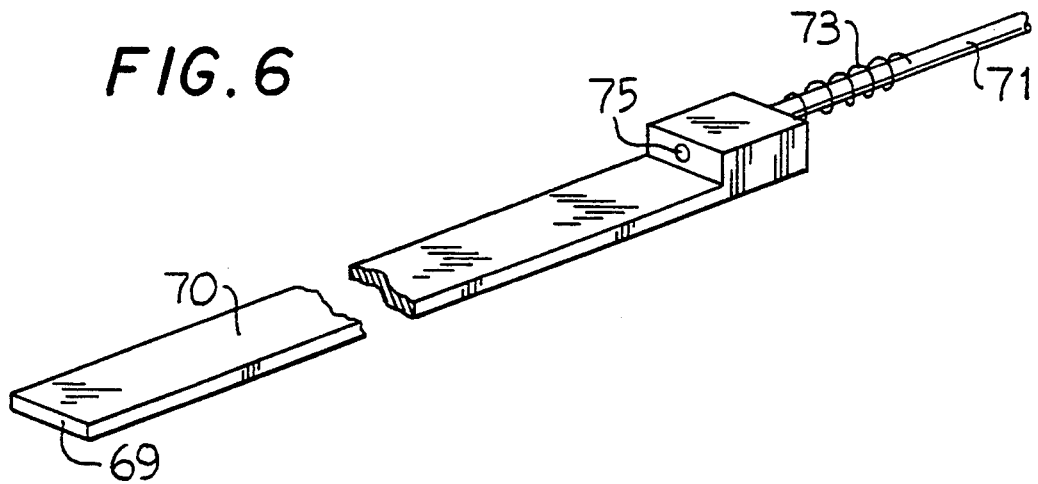
FIG. 6 is a sectional perspective view of the tension bar, the distal end of which is shown in FIG. 5.

With particular reference to FIGS. 5 and 6, a tension bar 70 has a forward surface 69 and is configured to be received by the staple tray channel 78 such that when the tension bar 70 travels forward a series of nested staples 100 disposed therein are urged forward by the forward surface 69.

A rod 71 (shown in FIG. 6) is attached to the rear portion of the tension bar 70. An attachment aperture 75 provides access to a fastener or screw (not shown) disposed therein for attaching the rod 71 to the tension bar 70. A coil spring 73 disposed about the rod 71 urges the tension bar 70 forward such that it will cause a series of nested staples 100 to move forward toward the jaws 62 and 64.

The rod 71 extends through the rear of the handle 20 such that the proximal end (not shown) thereof may be grasped and retracted against the urging of coil spring 73 such that staples 100 may be loaded through the opening 66 into the staple tray 72 as discussed in further detail below. The proximal end of the rod 71 may be knurled or have a knob formed thereon to facilitate grasping.

Having thus described the structure of the improved staple 100 and endoscopic stapler 10 of the present invention, the operation thereof will be discussed in detail with reference to FIGS. 8 through 13 below.

Figure 12:
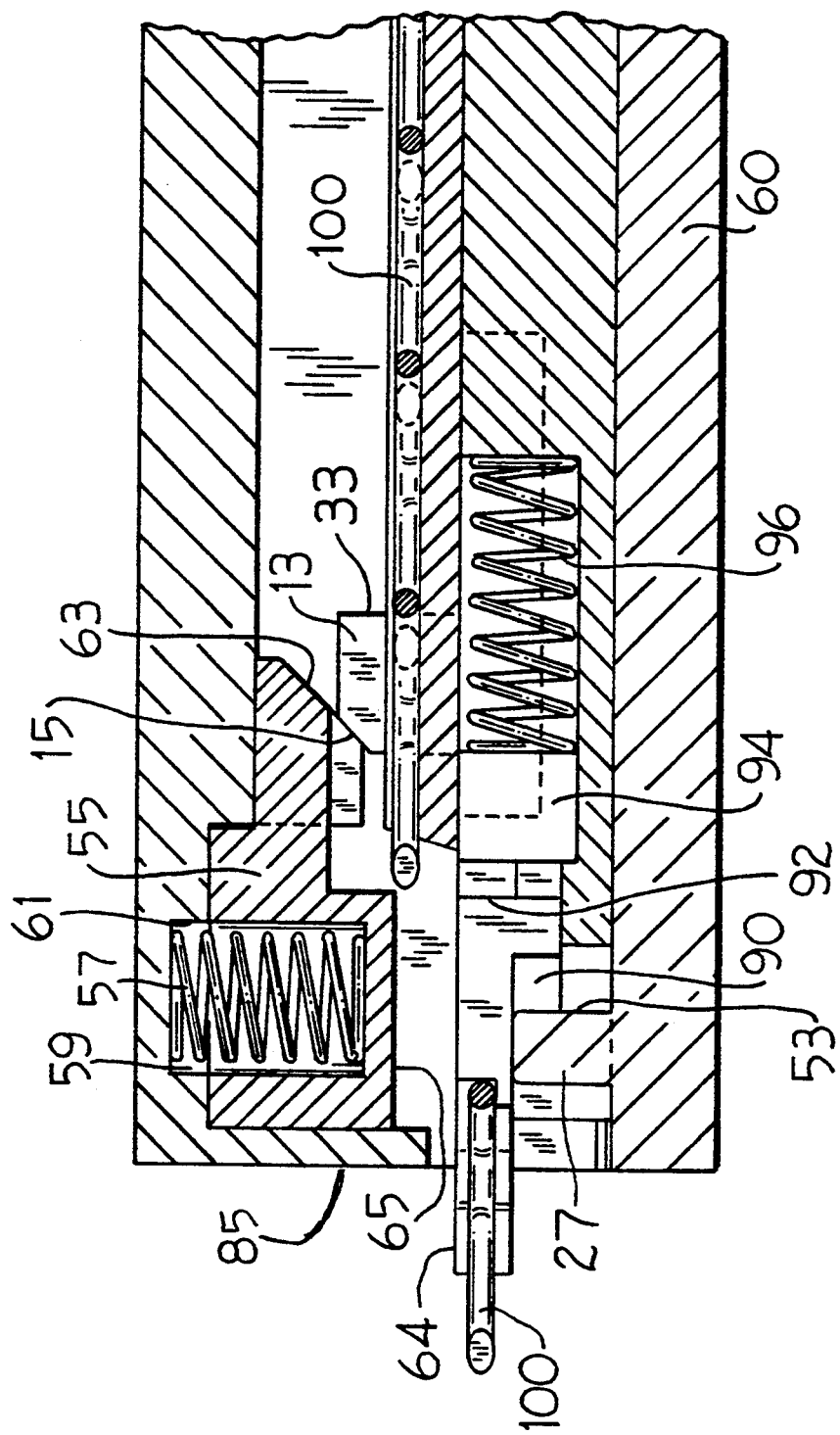
FIG. 12 is a cross sectional side view of the endoscopic stapler of FIG. 11, additionally showing the upper half thereof, with the extensible jaws disposed in their extended position.

With particular reference to FIGS. 8, 11 and 12 the lower half of the distal portion 81 of the tubular member 18 is shown having the jaws partially extended and showing a series of nested staples 100 disposed within the staple tray 72 such that they may be fed forward or digitally toward the extensible jaws 62 and 64. A staple 100 is shown disposed within the jaws 62 and 64. The jaw carrier 31 has moved sufficiently forward for the closure camming surface 90 of the jaws 62 and 64 to contact the jaw closing cam 27 such that further forward motion will cause the jaw closing cam 27 to cam into a closed or crimping position.

When the distal end 81 of the tubular member 18 is placed in contact with the anatomical body portion or therapeutic device to be stapled and the trigger 22 is partially depressed or actuated, the staple 100 is forced into the anatomical body portion or therapeutic device as the jaws 62 and 64 extend to the point illustrated in FIG. 8. Further, depression or actuation of the trigger 22 causes the jaws to move further forward such that the jaw closing cam 27 cams against the closure camming surface 90 of the jaws 62 and 64, thereby affecting crimping of the staple 100.

In FIG. 8 a nested series of improved surgical staples 100 of the present invention are shown (in phantom) disposed within the staple tray 72. The staples 100 are nested since a portion of a previous (forward) staple is disposed within or between the arms of a subsequent (rear) staple 100.

Figure 10:
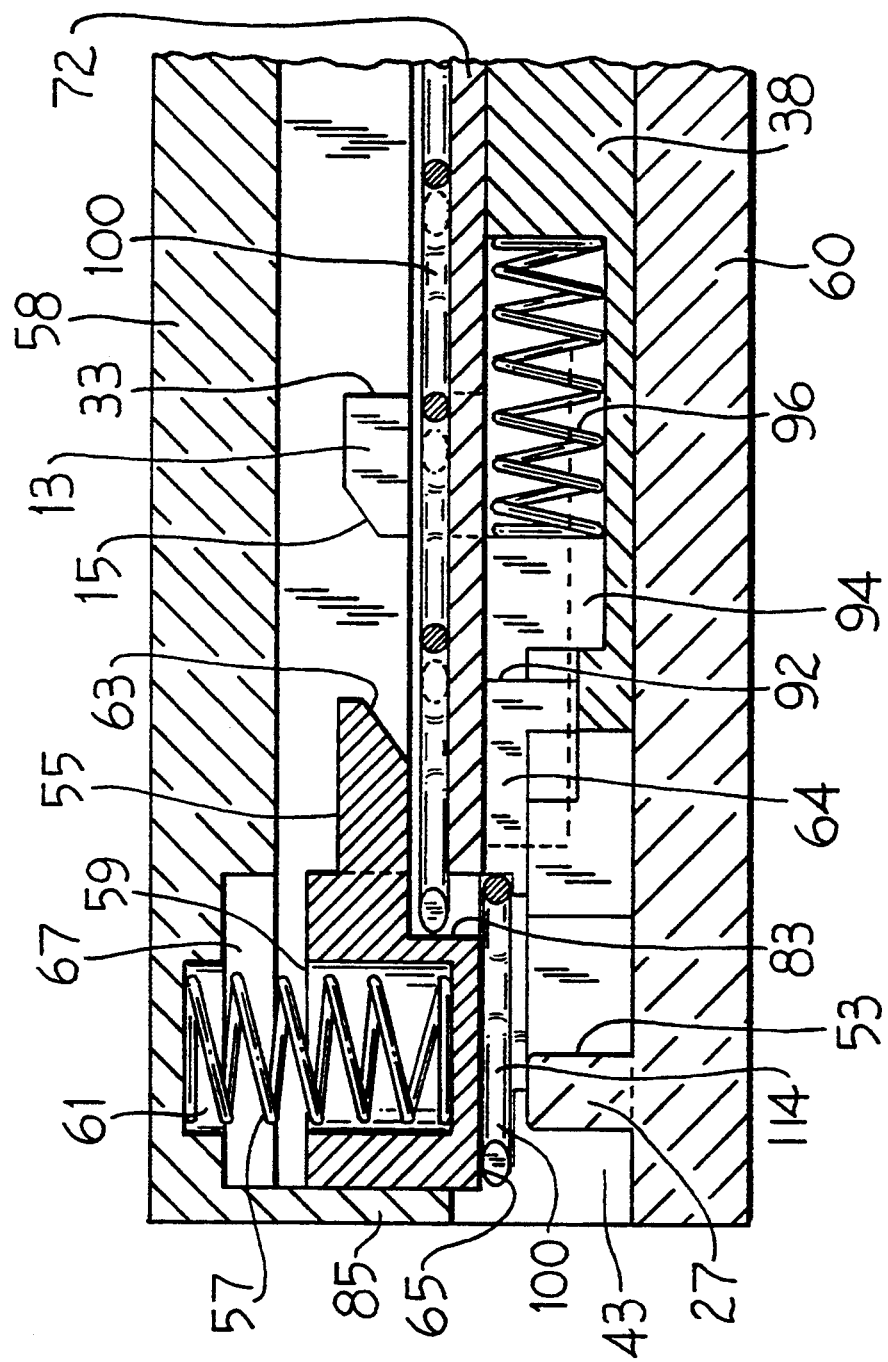
FIG. 10 is a cross sectional side view of the distal end portion of FIG. 9, additionally showing the upper half thereof;.

With particular reference to FIGS. 9 and 10, the distal end 81 of the tubular member 18 is shown with the extensible jaws 62 and 64 fully retracted into the channel 43 as they would be prior to depressing or actuating the trigger 22. In this configuration, the tips 104 of the forward most staple 100 disposed within the staple tray 72 abut the staple abutment surface 83 of the staple pressure plate 55 such that further forward movement of the series of nested staples 100 under the urging of the tension bar 70 (shown in FIGS. 5 and 6) does not occur.

Depression or actuation of the trigger 22 will cause the push rod 38 to move forward thus causing the staple 100 disposed within the jaws 62 and 64, to extend from the opening 66 formed in the lower tubular member housing.

The spring biased jaw opening cam 94 (best shown in FIG. 5) is biased towards and contacts the opening camming surfaces 92 of the jaws 62 and 64. Thus, the spring biased jaw opening cam 94 would maintain the opened or spread apart positioning of the jaw 62 and 64 even if no staple 100 were presently disposed therein. This assures that the extensible jaws 62 and 64 will be positioned to accept the next or forward most staple 100 from the staple tray 72 after the staple 100 presently disposed within the extensible jaws 62 and 64 is dispensed.

The camming surfaces 15 of the arms 11 and 13 do not contact the camming surface 63 of the staple pressure plate 55 (as best shown in FIG. 10). Thus, the staple pressure plate 55 is free to travel downward under the urging of spring 57 such that it contacts the upper surface of staple 100 disposed within the extensible jaws 62 and 64.

With particular reference to FIGS. 11 and 12, the distal end 81 of the tubular member 18 is shown with the extensible jaws 62 and 64 partially extended from the channel 43 as they would be after partially depressing or actuating the trigger 22. In this configuration the staple pressure plate 55 has been cammed upward by the push rod arms 11 and 13. The staples 100 disposed within the staple tray 72 can move distally under the urging of spring 73 until the distal most staple 100 abuts lip 85. Thus, the distal most staple 100 from the staple tray 72 may be urged downward into the extensible jaws 62 and 64 when the jaws 62 and 64 retract.

The closing camming surfaces 90 of the extensible jaws 62 and 64 has just contacted the jaw closing cam 27 in FIGS. 11 and 12. Further depression or actuation of the trigger 22 would thus cause closing or crimping of the extensible jaws wherein the tips 104 of the staple 100 would be forced toward each other as the extensible jaws 62 and 64 move into their fully extended positions.

Figure 13:
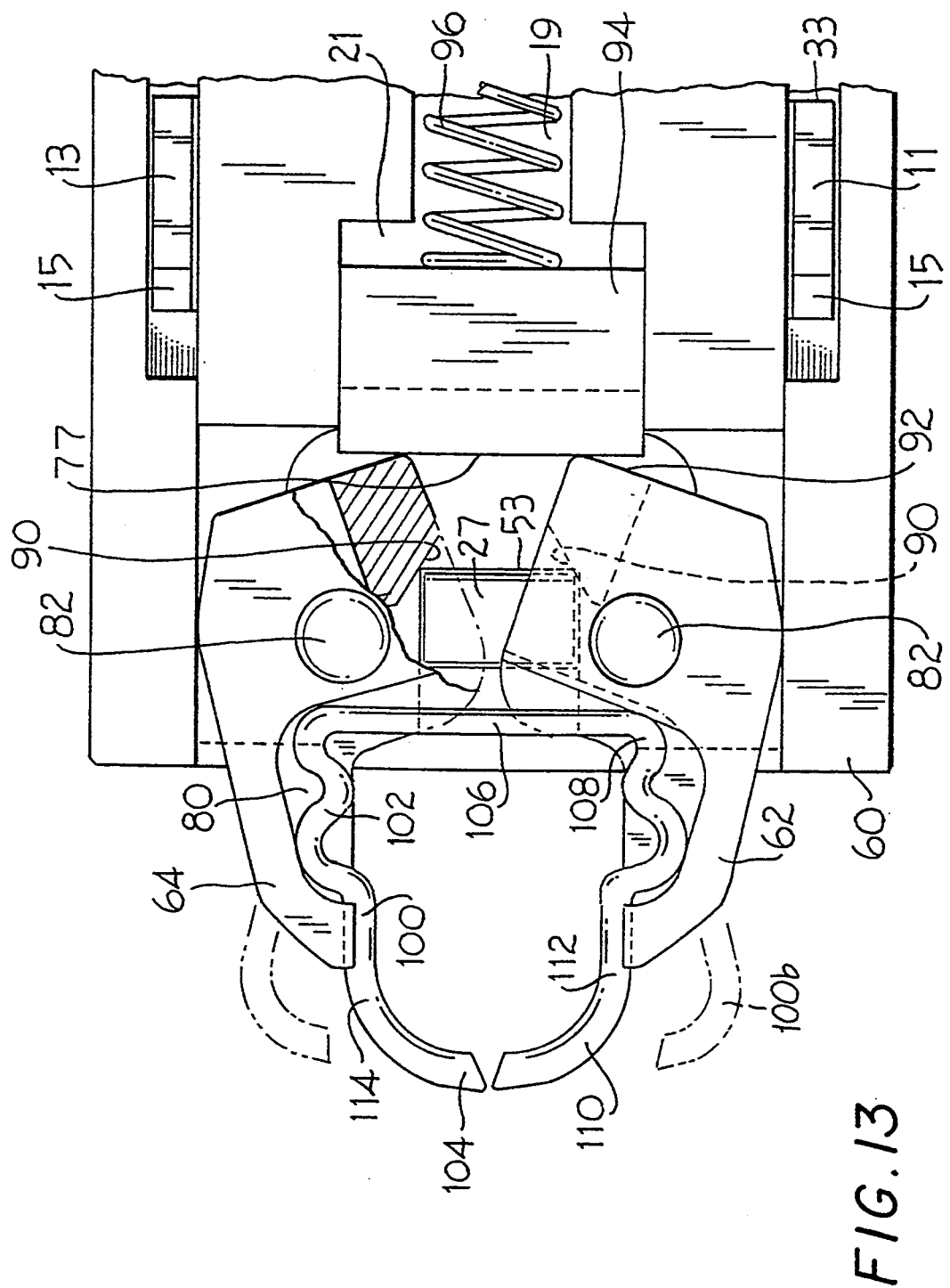
FIG. 13 is an enlarged top plan view of the lower half of the distal end of the endoscopic stapler of FIG. 11 illustrating the crimping action thereof, an uncrimped staple being shown in phantom lines and a crimped staple being shown in solid lines.

With particular reference to FIGS. 13, the crimping action of the jaws 62 and 64 is depicted. Forward movement of the jaw carrier 31 forward of the position illustrated in FIGS. 8, 11 and 12 causes the closure camming surface 90 of the jaws 62 and 64 to abut and cam against the jaw closing cam 27 such that the tips 104 Of a staple 100 disposed within the jaws 62 and 64 move toward each other from the position shown in phantom 100b to the position shown in solid lines 100.

The camming action causes the jaws 62 and 64 to rotate against the urging of spring biased jaw opening cam 94, thereby forcing the jaw opening cam 94 backwards slightly against the urging of spring 96. The jaw opening cam 94 will urge the jaws 62 and 64 into an open position when the jaws retract into the tubular member 18 as the trigger 22 is released.

The amount of crimping action applied to the staple 100 by the jaws 62 and 64 is determined by the positioning of the trigger stop screw 54 (shown in FIG. 3) which limits the backward travel of the trigger 22 and thereby likewise limits the forward travel of the push rod 38. The trigger stop screw 36 can be adjusted by placing the blade of a flat tip screwdriver within the slot 54 formed therein and rotating. Aperture 56 is provided in the rear of the handle 20 to provide access to the slot 54 of the trigger stop screw 36. Thus, adjustment of the trigger stop screw 36 determines the amount which jaws 62 and 64 rotate as they are cammed by jaw closing cam 27.

With the jaws 62 and 64 in their extended position, the camming surface 15 of the arms 11 and 13 contact the camming surfaces 63 of the stapler pressure plate 55, thus urging the staple pressure plate 55 upward. Releasing the trigger 22 causes the extensible jaws 62 and 64 to retract within the tubular member 18 to the position shown in FIGS. 9 and 10 such that the forward most staple disposed within the staple tray 72 may be loaded into the jaws 62 and 64. Rearward movement of the jaw carrier 31 causes the camming surfaces 15 of the arms 11 and 13 to cease camming the camming surface 63 of the staple pressure plate 55 such that the staple plate 55 is permitted to be urged downward by coil spring 57.

With the jaws 62 and 64 in their extended position the forward most staple 100 in the staple tray 72 is free to travel forward such it will be positioned to be received by the jaws 62 and 64 when the trigger 22 is released and the jaws 62 and 64 retract. Thus, when the jaws 62 and 64 retract, the pressure plate 55 is permitted to urge the forward most staple into position such that it is received by the jaws 62 and 64.

The endoscopic staples of the present invention may be fabricated primarily of plastic and pre-loaded with staples at the time of manufacture such that it can be sold as a disposable item. Thus, there would be no need to refill the endoscopic stapler with staples. Alternatively, the endoscopic stapler could be fabricated of a more durable material, i.e. stainless steel, and disassembled, autoclaved, re-loaded with staples, and reassembled as required. Additionally, other forms of loading the endoscopic stapler are contemplated.

It is understood that the exemplary improved surgical staple and the endoscopic stapler described herein and shown in, the drawings represents only presently preferred embodiments of, the invention. Indeed, various modifications and additions may be made to such embodiments without departing from the spirit and scope of the invention. For example, the improved surgical staple need not be configured precisely as shown, but rather may utilize a variety of shapes that permit crimping and facilitate use with an endoscopic stapler. Thus, these and other modifications and additions may be obvious to those skilled in the art and may be implemented to adapt the present invention for use in a variety of different applications.

Also, a variety of mechanisms are contemplated for effecting movement of the push rod 38. Thus the present invention need not be limited to the trigger and linkage mechanisms depicted.

What is claimed is:

1. An endoscopic stapler for stapling body tissue, which comprises:
   a) an elongate member which supports a plurality of staples in nested fashion generally within a first plane, said elongate member having a distal end and being dimensioned to be received by a trocar;
   b) an actuating mechanism having a jaw carrier disposed proximate the distal end of said elongate member;
   c) a first jaw and a second jaw pivotally mounted on a distal end portion of said actuating mechanism, said first and second jaws each having a projection having a camming surface and positioned in a second plane offset from said first plane of said nested staples, said first and second jaws being adapted to receive a staple from within said elongate member so as to apply and crimp said staple to the body tissue;
   d) biasing means for individually urging said staples from said first plane of said nested staples toward said second plane of said first and second jaws and into said jaws; and
   e) camming means positioned proximate said distal end of said elongate member and having camming portions dimensioned and positioned for engagement by said camming surfaces of said first and second jaws upon distal movement of said jaws toward said camming means;

wherein actuation of said actuating mechanism causes said first and second jaws to move toward said camming means such that each said camming surface of each said jaw is urged against said camming means to thereby cause each said jaw to pivot around said camming means to move a distal end of one of said jaws toward a distal end of the other to crimp said staple positioned therebetween.

2. The endoscopic stapler as recited in claim 1 further comprising:

a channel sized and configured to receive said plurality of nested staples and to feed said staples toward said first and second jaws;

wherein said first and second jaws crimp a staple held therein and said channel feeds the staples received thereby in response to the actuation of said actuating mechanism.

3. The endoscopic stapler as recited in claim 2 wherein said actuating mechanism comprises:

a) a trigger; and b) a push rod attached to said trigger such that said push rod moves in response to actuation of said trigger, said push rod being attached to said jaws such that said jaws move longitudinally in response to motion of said push rod.

4. The endoscopic stapler as recited in claim 3 further comprising a pressure plate disposed within the distal end of said elongate member, said pressure plate being spring biased to urge staples from said channel into said jaws.

5. The endoscopic stapler as recited in claim 4 further comprising:

(a) a first camming surface formed on said push rod;

(b) a second corresponding camming surface formed on said pressure plate;

(c) wherein the motion of said push rod resulting from the actuation of said trigger causes said first and second camming surfaces to cooperate such that said pressure plate is urged away from said jaws to facilitate the feeding of a staple from said channel to said jaws.

6. The endoscopic stapler as recited in claim 5 further comprising:

a spring disposed proximate said jaws for biasing said jaws apart;

wherein longitudinal movement of said jaws causes said camming means and said projections to cooperate to urge said jaws together against the bias of said spring.

7. The endoscopic stapler as recited in claim 6 further comprising an adjustment means disposed within said stapler for limiting the movement of said trigger such that the amount of crimp applied to a staple may be selectively varied.

8. The endoscopic stapler as recited in claim 7 further comprising a spring for urging said plurality of nested staples through said channel toward said jaws.

9. The endoscopic stapler as recited in claim 8 wherein the outer diameter of said elongate member is less than one centimeter.

10. The endoscopic stapler as recited in claim 1 wherein said actuating mechanism includes an axially movable member for mounting said first and second jaws such that actuation of said actuating mechanism causes said mounting member to move said jaws into engagement with said camming means.

11. A surgical staple for use in surgical procedures, which comprises:

a) a base portion formed of a length of wire having first and second ends;

b) an arm extending from each end of said base portion, each of said arms having a distal end portion bent inwardly toward the other at a first angle relative to said arm, such that a distal end of said inwardly bent distal end portion extends inwardly toward a distal end of the opposing inwardly bent distal end portion, each said inwardly bent distal end portion having a beveled end surface oriented at a second angle relative to a longitudinal axis of said inwardly bent distal end portion, said second angle being such that when said arms are applied to body tissue and moved inwardly so as to contact each other, each said end surface contacts the other in confronting relation therewith; and c) abutment means extending outwardly of each said arm at a location between said respective end of said base portion and said inwardly bent distal end portion of said arm wherein a plurality of said base portions may be positioned in a row in series nested relation for application of said associated arms to body tissue said abutment means configured and dimensioned to prevent said arms associated with said base portion from overlying said arms extending from an adjacent staple base portion so as to prevent premature closure thereof.

12. An endoscopic stapler for stapling body tissue which comprises:

a) an elongate member which support a plurality of staples in nested fashion, said elongate member having a distal end and dimensioned to be received by a trocar;

b) a longitudinally movable actuating mechanism having a jaw carrier disposed proximate the distal end of said elongate member;

c) a first jaw and a second jaw pivotally mounted on the jaw carrier of said actuating mechanism, said first and second jaws having projections each having a camming surface portion and adapted to receive a staple from within said elongate member so as to apply and crimp said staple to the body tissue;

d) biasing means for individually urging said staples from said elongate member into said first and second jaws; and e) at least one camming means having camming portions and positioned on said elongate member proximate said distal end and at a location which interacts with said camming projections of said jaws when said jaws are moved distally wherein said camming surface portions of said jaws interacts with said camming portions of said camming means to cause said jaws to pivot to crimp each said staple positioned therein whereby the distal ends of said staples are individually crimped towards each other into confronting relation.

13. The endoscopic stapler as recited in claim 12 wherein said actuating mechanism includes a longitudinally movable member for mounting said first and second jaws such that actuation of said actuating mechanism causes said mounting member to move said jaws into engagement with said camming means.

14. An endoscopic stapler for stapling body tissue, which comprises:

a) an elongate member which supports at least one staple, said elongate member having camming means having camming portions and formed within said elongate member and proximate a distal end thereof, said elongate member dimensioned to be received by a trocar;

b) in actuating means having a jaw carrier disposed proximate the distal end of said elongate member;

c) a first jaw and a second jaw pivotally mounted on the jaw carrier of said actuating means, said first and second jaws each having a camming projection having a camming surface formed thereon, said first and second jaws being adapted to receive said at least one staple from within said elongate member, said first and second jaws being movable within said elongate member such that each said camming surface of each said jaw is urged against said camming portions of said elongate member to pivot each said jaw around said elongate member camming means to move a distal end of each one of said jaws toward a distal end of the other so as to apply and crimp said staple positioned between said jaws to the body tissue; and d) a biasing mechanism for individually urging said at least one staple toward said first and second jaws and into said jaws.

* * * * *